USO05533977A

United States Patent [19]
Metcalf et al.

[11] Patent Number: 5,533,977
[45] Date of Patent: Jul. 9, 1996

[54] TROCAR

[75] Inventors: Gerald L. Metcalf, Burnsville; Bradley C. Poff, White Bear Lake, both of Minn.; John M. Barker, Ventura, Calif.

[73] Assignee: Origin Medsystems, Inc., Menlo Park, Calif.

[21] Appl. No.: 400,460

[22] Filed: Mar. 7, 1995

Related U.S. Application Data

[63] Continuation of Ser. No. 182,537, Jan. 13, 1994, abandoned, which is a continuation of Ser. No. 958,964, Oct. 9, 1992, abandoned.

[51] Int. Cl.$^6$ .......................... A61M 5/178; A61M 25/00
[52] U.S. Cl. .......................... 604/164; 604/167; 604/264
[58] Field of Search .......................... 604/158, 161, 604/164–167, 170, 264, 272–274; 606/185, 190; 128/754

[56] References Cited

U.S. PATENT DOCUMENTS

| | | |
|---|---|---|
| 1,527,291 | 2/1925 | Zorraquin . |
| 2,001,638 | 5/1935 | Tornsjo . |
| 2,623,521 | 12/1952 | Shaw . |
| 2,630,803 | 3/1953 | Baran . |
| 3,399,674 | 9/1968 | Pannier et al. .......................... 604/165 |
| 3,713,447 | 1/1973 | Adair . |
| 3,774,604 | 11/1973 | Danielsson . |
| 3,789,852 | 2/1974 | Kim et al. . |
| 4,168,699 | 9/1979 | Hauser . |
| 4,177,814 | 12/1979 | Knepshield et al. . |
| 4,190,048 | 2/1980 | Sampson . |
| 4,403,617 | 9/1983 | Tretinyak . |
| 4,431,426 | 2/1984 | Groshong et al. . |
| 4,535,773 | 8/1985 | Yoon . |
| 4,543,966 | 10/1985 | Islam et al. .......................... 128/754 |
| 4,601,710 | 7/1986 | Moll .......................... 604/274 X |
| 4,613,329 | 9/1986 | Bodicky .......................... 604/165 |
| 4,617,929 | 10/1986 | Gill . |
| 4,617,933 | 10/1986 | Hasson . |
| 4,654,030 | 3/1987 | Moll et al. .......................... 606/185 X |
| 4,682,981 | 7/1987 | Suzuki et al. .......................... 604/158 |
| 4,747,831 | 5/1988 | Kulli . |
| 4,808,168 | 2/1989 | Warring . |
| 4,813,426 | 3/1989 | Haber et al. . |
| 4,902,280 | 2/1990 | Lander . |
| 4,906,236 | 3/1990 | Alberts et al. . |
| 4,922,602 | 5/1990 | Mehl . |
| 4,931,042 | 6/1990 | Holmes et al. .......................... 604/164 |
| 4,952,207 | 8/1990 | Lemieux . |
| 4,955,870 | 9/1990 | Ridderheim et al. . |
| 5,030,206 | 7/1991 | Lander .......................... 604/164 |
| 5,066,288 | 11/1991 | Deniega et al. .......................... 604/274 |
| 5,104,382 | 4/1992 | Brinkerhoff et al. .......................... 604/274 X |
| 5,114,407 | 5/1992 | Burbank . |
| 5,116,353 | 5/1992 | Green .......................... 604/164 X |
| 5,127,909 | 7/1992 | Schichman .......................... 604/272 X |
| 5,129,885 | 7/1992 | Green et al. .......................... 604/165 X |
| 5,152,754 | 10/1992 | Plyley .......................... 604/164 |

FOREIGN PATENT DOCUMENTS

| | | |
|---|---|---|
| 0135364 | 3/1985 | European Pat. Off. . |
| 0265193 | 4/1988 | European Pat. Off. . |
| 0479130 | 4/1992 | European Pat. Off. . |
| 0494520 | 7/1992 | European Pat. Off. . |
| 921554 | 4/1982 | U.S.S.R. . |
| 5,158,552 | 10/1992 | Borgia et al. .......................... 604/274 |

(List continued on next page.)

OTHER PUBLICATIONS

"The Source of Laparoscopic Innovation", by Origin Medsystems, Inc., four (4) pages, 1992.

*Primary Examiner*—John D. Yasko
*Assistant Examiner*—Laird J. Knights
*Attorney, Agent, or Firm*—Limbach & Limbach

[57] ABSTRACT

A trocar for placement in the lumen of a cannula to facilitate inserting the cannula through tissue is disclosed. The trocar has an improved trigger/obturator assembly wherein the trigger comprises tissue cam parts each having (a) planar outer surfaces, and (b) an arcuate end portion at the distal end of the trigger including a distal edge surface that is arcuate about an axis normal to the outer surfaces. The arcuate end portions intersect at edge surfaces which are obscured by the arcuate end portions.

17 Claims, 4 Drawing Sheets

FOREIGN PATENT DOCUMENTS

| | | | |
|---|---|---|---|
| 5,215,526 | 6/1993 | Deniega et al. | 604/164 |
| 5,263,937 | 11/1993 | Shipp | 604/164 |
| 5,267,965 | 12/1993 | Deniega | 604/164 |
| 5,374,252 | 12/1994 | Banks et al. | 604/158 |
| 5,385,552 | 1/1995 | Haber et al. | 604/167 |
| 5,399,167 | 3/1995 | Deniega | 604/164 |
| 5,431,635 | 7/1995 | Yoon | 604/165 |
| 5,441,041 | 8/1995 | Sauer et al. | 600/106 |
| 5,474,539 | 12/1995 | Costa et al. | 604/164 |

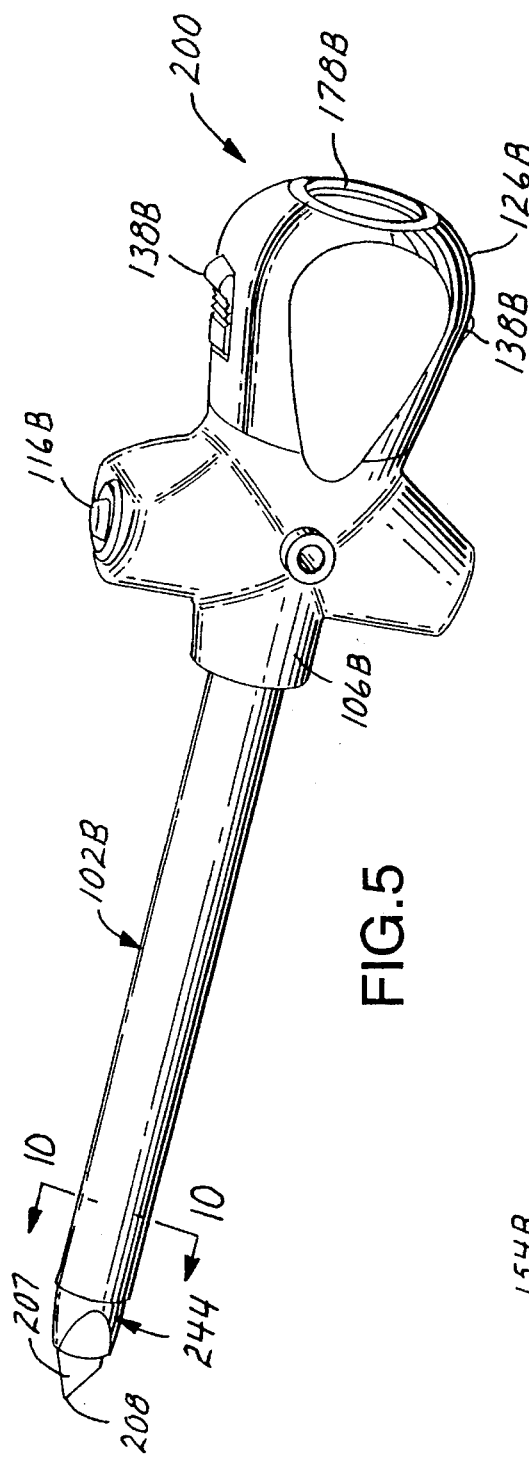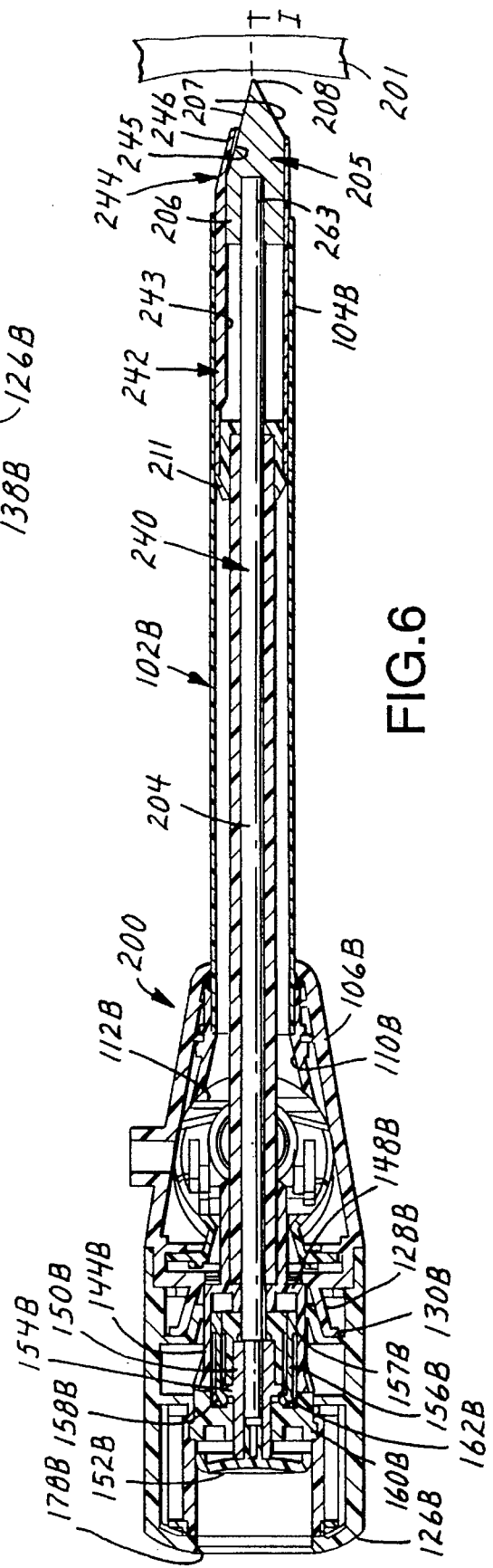

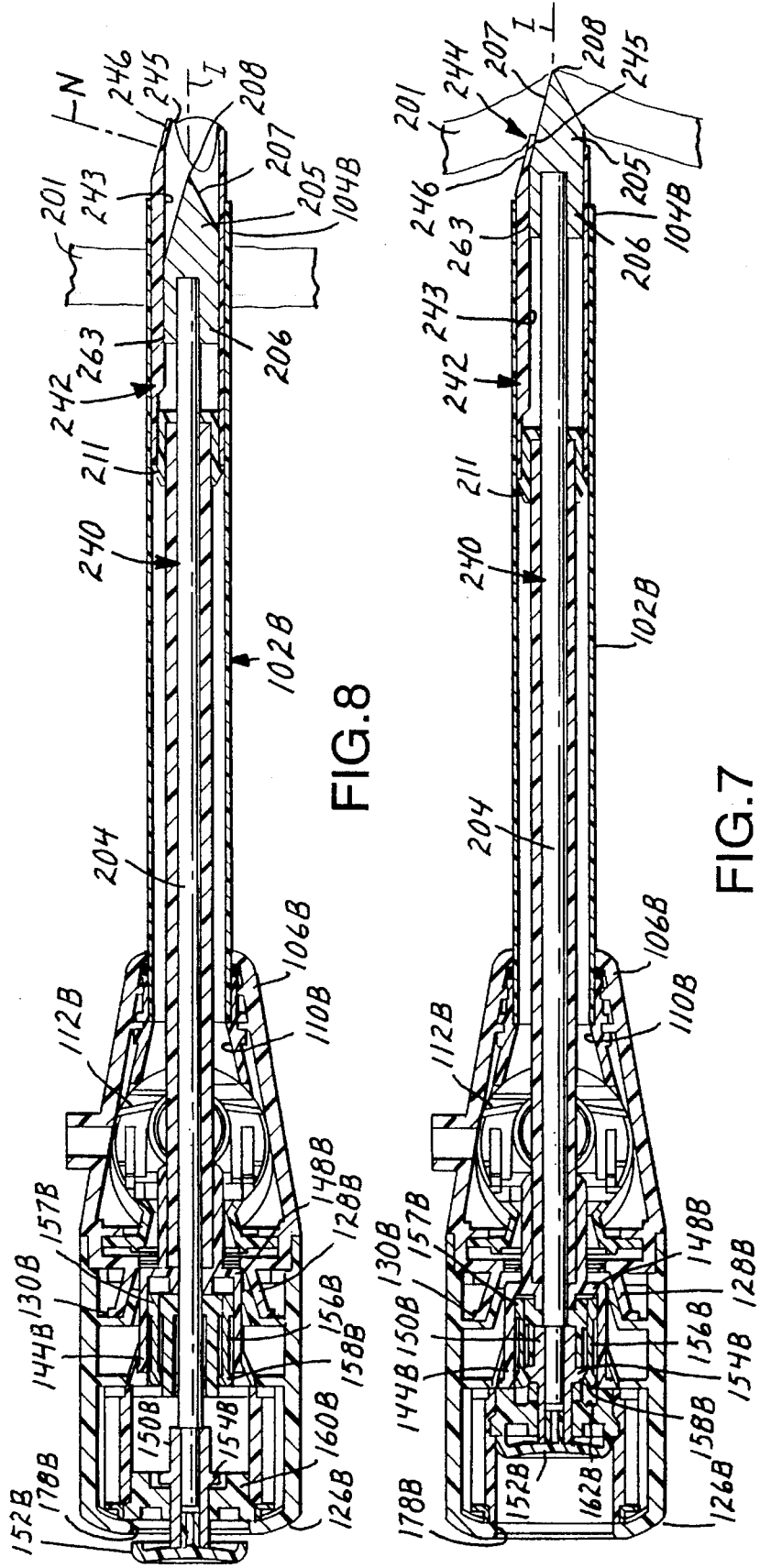

TROCAR

This application is a File-Wrapper continuation of U.S. patent application Ser. No. 08/182,537 (the '537 application), filed Jan. 13, 1994, now abandoned, which '537 application was a File-Wrapper continuation of U.S. patent application Ser. No. 07/958,964, filed Oct. 9, 1992, now abandoned.

TECHNICAL FIELD

The present invention is directed to trocars for inserting an access tube through an abdominal wall, and more particularly to a trocar having an improved obturator and trigger.

BACKGROUND OF THE INVENTION

An increasing number of abdominal surgical procedures are being performed with laparoscopic techniques in order to avoid a large skin incision. Typically in laparoscopic surgery, a special needle (a needle similar to the pneumoneedles described in U.S. Pat. No. 4,808,168 and U.S. patent application Ser. No. 07/808,152, both of which are herein expressly incorporated by reference) is inserted through the skin, and used to inflate the abdominal cavity with an insufflating gas such as carbon dioxide ($Co_2$). Once the abdomen is adequately dilated, the needle is removed and a rigid access tube or cannula with a diameter larger than the pneumoneedle (for example 5, 10 or 11 mm) is passed through the skin in the same location.

The access tube provides access for laparoscopes or other laparoscopic surgical tools such as the stapler described in U.S. Pat. No. 5,040,715 or the surgical clip appliers described in U.S. Pat. Nos. 5,084,057 and 5,100,420. To drive the access tube through the skin, the surgeon places a trocar in the lumen of the access tube to provide a sharp, leading edge for cutting tissue.

The art is replete with trocar devices, including those shown in U.S. Pat. Nos. 4,535,773, 4,601,710, 4,654,030, 4,902,280 and 4,931,042. Those trocars typically comprise an obturator with cutting surfaces for penetrating the skin, and a spring-loaded protective sleeve that surrounds the obturator. As these trocar devices are urged through the skin, friction with the skin causes the protective sleeve to slide proximally (rearwardly). After the access tube has penetrated through the skin, there is no longer friction between the protective sleeve and the skin, and the spring is designed to urge the protective sleeve distally (forwardly) to cover the cutting surfaces. Some of those trocars lock the protective sleeve in the forward position to reduce the risk of accidental puncture of the underlying organs.

These prior art trocars rely on a similar principle of operation: The friction or drag on the protective sleeve as the trocar is advanced through the skin pushes the protective sleeve back (proximally) to expose the cutting surfaces. Once the access tube has penetrated the skin, the drag on the protective sleeve is reduced and the sleeve accelerates distally (forwardly) under the bias of the spring to cover the cutting surfaces.

FIG. 1 illustrates a portion of a typical prior art trocar similar to the 10 mm Auto Suture Surgiport T.M., generally available from U.S. Surgical of Norwalk, Conn. That trocar includes an access tube 1, an obturator 2 and a shield 3. The shield 3 is biased distally to cover the obturator 2. The shield 3 comprises a generally cylindrical tube with a slightly rounded or angled end portion 4.

Existing trocars such as the trocar shown in FIG. 1 encounter problems because a significant amount of force usually must be applied to penetrate the skin (particularly the tough fascia). As a result of the significant insertion force, the trocar may continue to advance toward the underlying organs after it has penetrated the skin. Thus, the protective sleeve must "catch up" to the moving trocar point before the trocar reaches the underlying organs.

FIG. 2 illustrates another prior art trocar. This Figure generally illustrates a portion of trocar that is currently being sold in the United States under the name 10/11 mm Endopath™ (generally available from Ethicon of Somerville, N.J.). U.S. Pat. No. 5,066,288 to Deniega et al. describes a trocar similar to the trocar shown in FIG. 2. That trocar includes an access tube 5, an obturator 6 and a shield 7. The shield 7 is biased distally to cover the obturator 6. Unlike other trocars, the shield 7 of the trocar shown in FIG. 2 includes a bullet shaped end portion 8 comprising three semicircular lobes 9.

U.S. Pat. No. 5,066,288 states that the trocar restricts tissue trauma. However, like the trocar shown in FIG. 1, trocars similar to those shown in FIG. 2 also encounter problems because a significant amount of force is nevertheless required to penetrate the skin (particularly the tough fascia). Again, as a result of the significant insertion force, the obturator may continue to advance toward the underlying organs even after it has penetrated the skin.

FIGS. 3 and 4 illustrate yet another trocar similar to the trocar described in U.S. Pat. No. 4,654,030 to Moll. That trocar includes an access tube (not shown), an obturator 10 and shield 11 that is biased distally to cover the obturator 10. The obturator has a triangular base 12, and three generally equilateral triangular surfaces 13.

The shield 11 comprises three parabolically shaped bevels 14 which form a triangular shaped opening 15. The parabolically shaped bevels 14 intersect at three edges 16. While U.S. Pat. No. 4,654,030 states that the trocar shown in FIGS. 3 and 4 markedly reduces the force required to insert the trocar into body cavities, the trocar shown in FIGS. 3 and 4 is believed to suffer from several drawbacks including: (1) the shield 11 is believed to concentrate tissue trauma generally at the edges 16 during insertion into the body cavity resulting in undesirable tissue trauma at the incision site, (2) the shield 11 (particularly the edges 16) may become caught on tissue which restricts movement of the shield 11 relative to obturator 10, which is particularly undesirable after the obturator has pierced the abdominal wall; and (3) the edges 16 of the shield 11 may be relatively sharp and may expose the underlying organs to damage from contact with the edges 16 of the shield 11 itself.

U.S. Pat. No. 5,152,754 discloses a trocar comprising an obturator which retracts relative to the access tube just after the obturator pierces the tissue defining the body cavity. U.S. Pat. No. 5,152,754 is assigned to the assignee of the present invention.

BRIEF DESCRIPTION OF THE INVENTION

According to the present invention there is provided a trocar having an improved obturator and trigger which (1) affords an acceptable amount of force required to insert the trocar into the abdominal cavity, (2) restricts force concentrations (and tissue trauma) at the incision site due to the shape of the trigger; (3) obscures any potential sharp edges on the trigger to restrict the chances of the trigger catching tissue or other structures which may inhibit the trigger's movement relative to the access tube after the trigger has penetrated into the body cavity; (4) restricts damage to underlying organs due to the shape of the trigger; and (5) resists binding or rotation of the obturator relative to the trigger.

According to the present invention, there is provided an improved trocar assembly having a novel obturator and trigger. The trocar is placed in the lumen of a cannula to facilitate insertion of the cannula through tissue defining a body cavity.

The trocar comprises a handle, and an elongate obturator which extends from the handle. The direction of elongation of the obturator and its center define a longitudinal axis. The obturator comprises cutting surfaces for cutting and penetrating the tissue defining the body cavity, and a trigger having a plurality of tissue cams. Each tissue cam comprises an inner surface and an outer, generally planar surface situated at an angle relative to the longitudinal axis. Each tissue cam also has a distal end portion that is arcuate about an axis normal to the outer surface.

Each of the distal end portions of the trigger has a distal most point. The distal end portions of the tissue cams intersect at edge portions. The distal most points of the distal end portions are spaced distally from the edge portions.

Optionally, the trocar includes a mechanism for restricting rotation of the obturator relative to the trigger. Such a mechanism may comprise the trigger having a detent member, and the obturator having a generally cylindrical base portion having a chamfered edge that engages the detent member.

Preferably, the trigger is mounted around the obturator. The trigger is adapted to move longitudinally and axially movement relative to the obturator. The trigger retracts proximally relative to the obturator as the trocar is advanced through the tissue defining the body cavity. The trigger advances distally after the cannula has penetrated through the tissue defining the body cavity.

Also, preferably, the trocar includes a mechanism for retracting the obturator proximally relative to the cannula after the obturator has cut the tissue defining the body cavity. More preferably, the obturator retracts proximally after the trigger advances distally.

Alternatively but not preferably, the present invention may comprise a trocar comprising an obturator defining a longitudinal axis and a protective sleeve having a plurality of tissue cams. The protective sleeve's tissue cams each have an inner surface and an outer, generally planar surface situated at an angle relative to the longitudinal axis. Each of the protective sleeve's tissue cams also have a distal end portion that is arcuate about an axis normal to the outer surface. Preferably, the distal end portions of the tissue cams intersect at edge portions. Distal most points of the distal end portions are spaced distally from the edge portions of the protective sleeve.

BRIEF DESCRIPTION OF THE DRAWINGS

The present invention will be further described with reference to the accompanying drawing wherein like reference numerals refer to like parts in the several views, and wherein:

FIG. 5 is a perspective view of a trocar assembly according to the present invention;

FIGS. 6 through 8 sequentially illustrate the operation of the trocar of FIG. 5 wherein:

FIG. 6 is a sectional view illustrating the relative positions of the obturator and trigger after a button of the trocar has been pressed and just prior to insertion into the abdominal cavity;

FIG. 7 is a sectional view illustrating the relative positions of the obturator and trigger as the trocar just begins to pierce the tissue defining the body cavity;

FIG. 8 is a sectional view illustrating the relative positions of the obturator and trigger after the obturator has pierced the tissue defining the body cavity and after the obturator has retracted relative to the trocar handle;

DETAILED DESCRIPTION OF THE PREFERRED EMBODIMENTS

Figure 1:
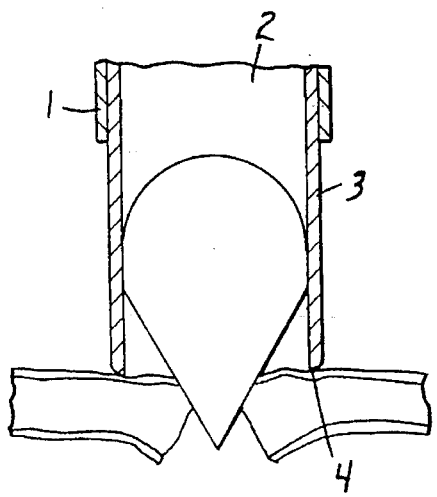
FIG. 1 is a partial side view of a prior art trocar illustrating penetration of tissue by the trocar.

Referring now to FIGS. 5 through 11 of the drawing there is shown an embodiment of a trocar device or assembly generally designated by reference character 200. The trocar 200 is similar to the trocar described in U.S. patent application Ser. No. 07/657,105, now U.S. Pat. No. 5,152,754, the entire contents of which are herein expressly incorporated by reference. Features of the trocar 200 that are similar to the features of the trocar described in U.S. Pat. No. 5,152,754 have been given the same reference character to which the suffix "B" has been added.

The trocar 200 includes the novel obturator and trigger according to the present invention. The trocar 200 facilitates insertion of a cannula through tissue defining a body cavity, for example inserting an access tube 102B through an abdominal wall 201. The access tube 102B comprises a cannula 104B that has an enlarged fixture 106B at its proximal end similar to the fixture 106 described in U.S. Pat. No. 5,152,754. There is an opening 110B at the proximal end of the chamber similar to the opening 110 in U.S. Pat. No. 5,152,754.

A trap door valve member 112B similar to trap door valve member 112 (in U.S. Pat. No. 5,152,754) is also present to close the opening 110B. The valve member 112B is operated by a pushbutton 116B similar to the pushbutton 116 (again further shown in U.S. Pat. No. 5,152,754).

The trocar 200 has a stopcock (not shown) by which pressurized gas (insufflating gas) can be provided to the chamber to maintain the gas pressure in the body cavity, and thereby keep the cavity inflated to facilitate the surgical procedure.

The trocar 200 comprises a handle or housing 126B that is releasably attached to the fixture 106B so that after the trocar 200 is used to insert the access tube 102B in the tissue defining the body cavity, the trocar 200 can be removed leaving the access tube 102B. The tube 102B can then be used to introduce surgical instruments into the body cavity.

The proximal end of the fixture 106B has a funnel-shaped extension 128B, with an enlarged rim 130B. Resilient fingers are also present and have a shoulder to engage the rim 130B and attach the handle 126B to the fixture 106B. The sides of the handle have two pivotally mounted buttons 138B which operate similar to the buttons 138 described in U.S. Pat. No. 5,152,754.

The trocar 200 also includes an obturator 240 extending from the distal end of the handle 126B. Note FIGS. 6–8. The direction of elongation of the obturator 240 and its center defines an imaginary, longitudinal axis I. The trocar also includes trigger 242 mounted around the obturator 240 for axial movement relative to the obturator 240. The trigger 242 is preferably mounted so that it can retract proximally relative to the obturator 240 in response to drag from the tissue 201 defining the body cavity as it is advancing through the tissue 201. The trigger can then advance distally after the cannula or access tube 102B has penetrated through the tissue 201 and reduced the drag on the trigger 242.

The obturator 240 comprises proximal 204 and distal 205 end portions. The distal end portion 205 comprises a base part 206 and also has generally planar surfaces 207 (preferably three) intersecting to form cutting edges or surfaces (again preferably three) and a point 208 at the distal most end of the obturator. The axis I is generally parallel to the direction of elongation of the obturator 240 and passes through point 208.

Trigger 242 has proximal and distal end portions with the proximal end portion attached to trocar adapter 211. Unlike trigger 142 shown in U.S. Pat. No. 5,152,754, the distal end of the trigger 242 comprises three tissue cams 244. Each of the tissue cams 244 has an inner surface 245 and a planar outer surface 246 situated generally at an angle relative to the longitudinal axis I. Preferably, the included angle between the outer surface 246 and the axis I is between about 10 degrees and about 40 degrees. Most preferably, the angle is about 15 degrees.

The cams 244 are believed to beneficially reduce the insertion force required to insert the trocar 200 through the abdominal tissue 201. The cams 244 each include a novel arcuate end portion 250 that is arcuate about an axis N normal to the outer surface 246 (See FIG. 8).

For example, when the trocar 200 is used to insert a cannula 104B having an lumen interior diameter of about 10 millimeters, the radius of curvature of the arcuate end portion 250 should be between about 0.18 inches and about 0.32 inches, and preferably approximately 0.25 inches.

The distal end portions 250 each have a distal most point 252. The distal end portions 250 of the cams 244 intersect at edge portions 255. The distal most points 252 of the distal end portions 250 are spaced distally (relative to the fixture 106B) from the edge portions 255.

Figure 4:
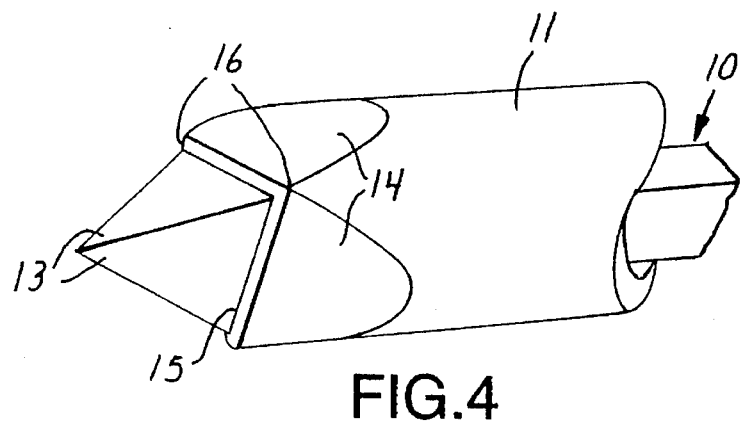
FIG. 4 is a perspective view of the obturator of FIG. 3 assembled with a sleeve in a retracted position.
Figures 9, 10:
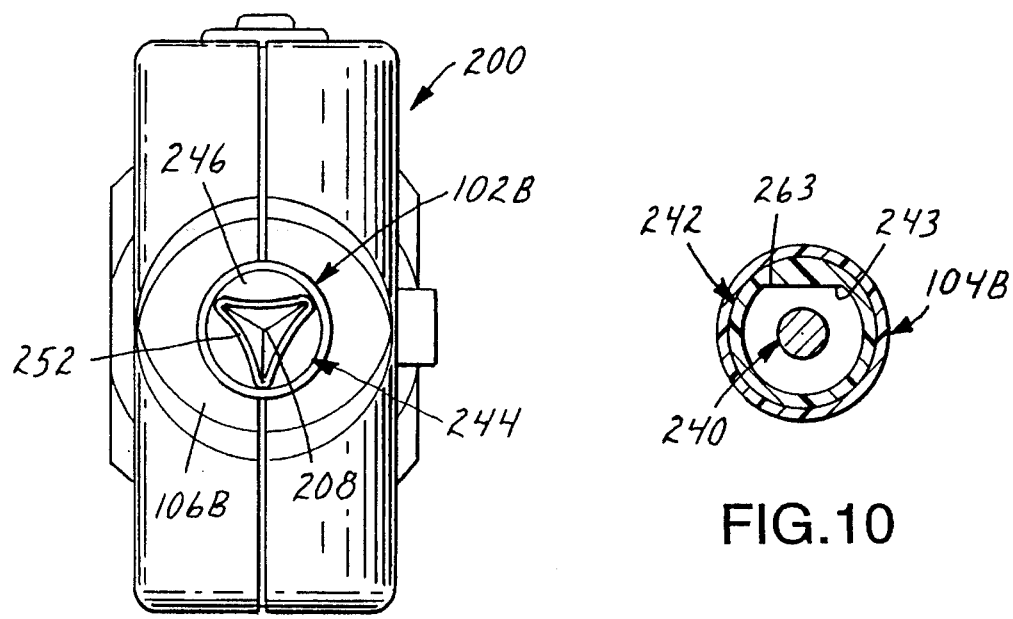
FIG. 9 is an enlarged end view of the trocar assembly of FIG. 5.
FIG. 10 is a sectional view of the trocar assembly of FIG. 5 taken approximately along lines 10—10 of FIG. 5 and with portions broken away to emphasize detail.
Figure 11:
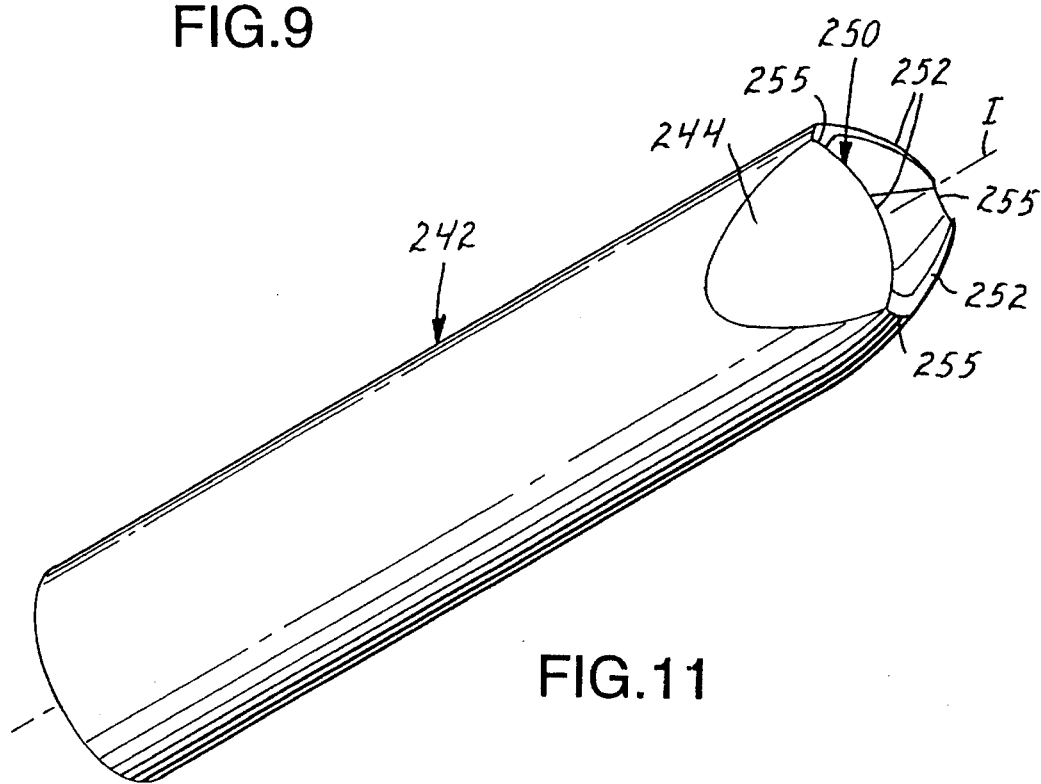
FIG. 11 is an enlarged perspective view of the novel trigger forming a portion of the present invention having portions broken away to emphasize details.

While not desiring to be bound by any particular theory, it is believed that the arcuate end portions 250 distribute the insertion force applied to the tissue 201 by the trigger 242 more evenly, than for example, a structure as shown in FIG. 4. The arcuate end portions 250 thus restrict trauma to the tissue 201. Additionally, the arcuate distal end portions 250 of the trigger 242 are believed to (1) obscure any potential sharp edges on the trigger 242 (e.g. portions 255) (2) restrict the opportunity for the trigger 242 to catch tissue which may inhibit the trigger's distal movement after it has penetrated into the body cavity; and (3) restrict damage to underlying organs due to the blunt shape of the end 250 itself. Unlike prior art trocars, the potentially sharp portions 255 are obscured by the arcuate end portions 250. The arcuate end portions 250 restrict damage to underlying organs from contact with the trigger itself.

The trocar 200 optionally includes means for restricting rotation of the obturator 240 relative to the trigger 242. That means may comprise the trigger 242 having inner and outer surfaces with the inner surface having a detent portion 243 (Note FIG. 6). The means also includes the base part 206 of the obturator provided in a generally cylindrical shape with a chamfered edge 263 (Note FIG. 10) for engaging the detent member 243 of the trigger 242. The means described in this paragraph is believed to restrict binding or rotation of the obturator and/or trigger relative to the housing of the trocar 200.

The trigger 242 is resiliently biased distally (relative to the housing or handle 126B). In the embodiment shown in FIGS. 5–11, the trigger 242 is biased with a spring (not shown), similar to the coil spring 146 shown in U.S. Pat. No. 5,152,754. The distal end of the spring (not shown) is supported on an internal shoulder 148B on the trigger, and its proximal end engages a raised shoulder on the obturator (described in more detail below).

The action of the spring (not shown but similar to spring 146 in U.S. Pat. No. 5,152,754) resiliently biases the trigger 242 distally. However, the trigger can move proximally against the bias, under the forces applied by the tissue defining the body cavity as the trocar 200 is advanced through the tissue 201. The trigger 242 has a "resilient" characteristic and moves distally when the applied forces are removed, as occurs once the access tube 102B is inserted through the tissue 201 and the trigger 242 is no longer in frictional contact with the tissue 201.

The trocar 200 also comprises means for retracting the point 208 on the obturator 240 relative to the cannula 104B after the point has penetrated through the tissue 201, thereby reducing the risk that the point 208 will cause damage inside the body cavity.

In trocar 200, the retracting means is triggered upon the distal (forward) movement of the trigger 242. When the novel obturator 240 and trigger 242 are used with the trocar 200, it is important that the trigger move distally so that the retracting means of the trocar 200 may operate. The arcuate surface portions 252 obscure the relatively pointed structures 255 to restrict the chances that the trigger 242 will catch tissue which might prevent the trigger 242 from moving distally and "triggering" the retracting means.

Like the embodiment shown in U.S. Pat. No. 5,152,754, in the trocar 200, there is a tubular extension 150B secured on a shoulder on the proximal end of the obturator 240. An enlarged head 152B is secured onto the proximal end of the extension 150B. The extension 150B has a generally radially extending flange 154B. The distal surface of the flange 154B forms the shoulder that engages the proximal end of the spring (not shown). Preferably four proximally extending resilient fingers 156B are disposed around the obturator.

The proximal ends of the fingers 156B have beads 158B that can engage the flange 154B on the extension 150B, and thereby hold the obturator against proximal retraction under the bias of spring (not shown but similar to spring shown in U.S. Pat. No. 5,152,754). The distal ends of the fingers 156B are anchored to a ring 157B. The ring 157B is supported on a generally cylindrical base similar to the base 159 shown in U.S. Pat. No. 5,152,754.

Before use, as shown in FIG. 6, the beads 158B on the fingers 156B engage the flange 154B, holding the spring (not shown) in compression and holding the obturator 240 from proximal retraction. A locking member 160B, slidably mounted on the proximal portion of the extension member 150B, locks the fingers 156B in engagement with the flange 154B. The bottom edge of the locking member 160B has notches 162B which, when the locking member 160B is in its distal most position, receive and engage the fingers 156B and hold the beads 158B in engagement with the shoulder.

The cylindrical section 144B of the trigger 242 is sized and positioned to engage the locking member 160B, and slide the locking member proximally as the trigger 242 slides proximally (as occurs as the trocar 200 is advanced through the tissue 201 and the friction of the tissue acts against the trigger 242).

As shown in FIGS. 6–7, when the trigger 242 moves proximally, it pushes the locking member 160B proximally. Thereafter, further proximal movement of the trigger 242 moves the locking member 160B. The cylindrical section 144B of the trigger 242 is sized to engage the fingers 156B, and hold the beads 158B in engagement with the flange 154B after the locking member 160B has been displaced. Thus, as shown in FIG. 7, when the trigger 242 is in its fully retracted position, the locking member 160B has been moved proximally, and the walls of the cylindrical section 144B hold the fingers 156B in engagement with the flange 154B.

The mechanism of the trocar 200 is now primed so that any distal advancement of the trigger 242 will cause the trocar 200 to retract the obturator point 208. Thus, the importance of permitting this distal advancement is apparent.

When the cannula 104B of access tube 102B pierces through the tissue 201, it shields the trigger 242 from contact with the tissue 201, and thus the tissue 201 no longer exerts frictional force on the trigger 242. The reduction in force on the trigger allows the trigger 242 to advance distally under the bias of the spring (not shown). This distal advancement is believed to be facilitated by the shape of the cams 244 of the trigger 242.

As the trigger 242 advances, the cylindrical section 144B releases the fingers 156B. When the fingers 156B are released, they spring resiliently outwardly, and the beads 158B clear the flange 154B. This allows the obturator 240 to retract under the bias of the spring (not shown).

As the obturator 240 retracts, it moves the locking member 160B with it. Moreover, the cap 152B protrudes through an opening in the handle 126B providing a visible signal, as well as a tactile signal that the obturator point 208 has retracted.

As shown in FIG. 8, the point 208 of the obturator retracts relative to the cannula 104B to a retracted position. Alternatively, the point 208 of the obturator may be designed to retract completely within the lumen of the cannula 104B so that the tip is located proximally relative to the distal end of the cannula 104B. This may conveniently be accomplished by increasing the length of travel of flange 154B between the position shown in FIG. 7 and the position shown in FIG. 8.

Operation

The operation of the trocar will now be described with reference to FIGS. 6 through 8 which sequentially illustrate the operation of the trigger. The trocar 200 optionally includes a protective cap (not shown) over the point 208 that is removed prior to use of the trocar 200. The access tube 104B is already installed over the distal end of the trocar 200. The user grasps the handle of the trocar 200, with the palm of the hand over the proximal end.

The trocar 200 is advanced against the tissue 201 defining a body cavity, for example the abdomen. The arcuate end surfaces 252 are believed to distribute the insertion force applied by the trigger 242 to the tissue 201 over a greater area than would, for example, a flat, planar surface. The shape of the arcuate end surface 252 is also believed to restrict force concentrations on the tissue 201 to thereby restrict tissue trauma.

As the trocar 200 is advanced, friction or drag from the skin urges the trigger 242 proximally. As the trigger 242 moves proximally, its enlarged proximal end also moves proximally.

The proximal end of the trigger 242 pushes the locking member 160B proximally, releasing the notches 162B from their engagement with the fingers 156B, while the enlarged end of cylindrical section 144B simultaneously moves over the fingers to continue to hold the beads 158B in engagement with the shoulder (Compare FIGS. 6 and 7). The user continues to advance the trocar, penetrating the tissue 201.

Once the cannula 104B has penetrated through the tissue 201, the drag on the trigger 242 is reduced, and the spring (not shown) urges the trigger 242 distally. The distal motion of the trigger 242 also causes the enlarged end to move distally, releasing the fingers 156B. The fingers 156B are displaced radially outwardly, releasing beads 158B from their engagement with the shoulder. This allows the spring (not shown) to expand, pushing the obturator 240 proximally (Compare FIGS. 7 and 8). Thus the point 208 begins to move proximally, i.e., it retracts.

The proximal motion of the point 208 causes the point to be quickly moved away from the underlying organs. As the obturator retracts, the proximal end of the button 152B projects through the opening in the handle, nudging the palm of the user and providing a positive tactile signal that the trocar has penetrated the tissue 201. Thus the user will have information as to when to stop advancing the trocar 200.

The user then grasps the fixture 106B of the access tube 102B, and pulls the trocar proximally, leaving the access tube 102B in the abdominal tissue 201. As noted above, the access tube preferably has a trap-door valve that closes the cannula 104B when the trocar is withdrawn to prevent the escape of gas from the abdomen. The trocar can be quickly prepared for reuse (on the same patient) by pressing the enlarged end of the button 152B down through the opening 178B, until the beads 158B on the fingers 156B engage the shoulder 144B, and the notches 162B on the locking member 160B hold the fingers in place. Another access tube can be placed over the trocar 200, and the procedure repeated.

The present invention has been described above in relation to the trocar 200 which has a means for retracting the obturator 240 relative to access tubes 102B. However, alternatively, but not preferably, the present invention may be used in conjunction with a trocar with an obturator that remains relatively stationary with respect to its cannula. For example, the present invention may comprise a protective sleeve having the shape shown in FIG. 11. The protective sleeve shown in FIG. 11 may be used, for example, to replace the protective sleeves shown in U.S. Pat. Nos. 4,535,773; 4,654,030; 4,931,042; and 5,066,288, the entire contents of which are herein expressly incorporated by reference.

Insertion force tests were conducted using an obturator and four different shaped structures. The insertion force for the four structures was separately measured through two different materials: 1. a 0.125 inch membrane of Neoprene™, and 2. a 0.030 inch membrane of Polyurethane. The structures were sized to approximate a protective sleeve or trigger for a 10 mm trocar. The location of insertion of the four tips into the membranes was randomly assigned.

Figure 2:
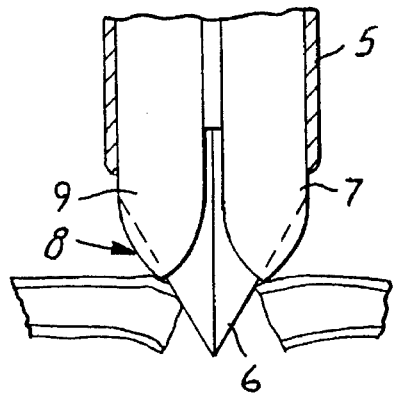
FIG. 2 is a partial side view of a second, bullet nosed prior art trocar illustrating penetration of tissue by the trocar.
Figure 3:
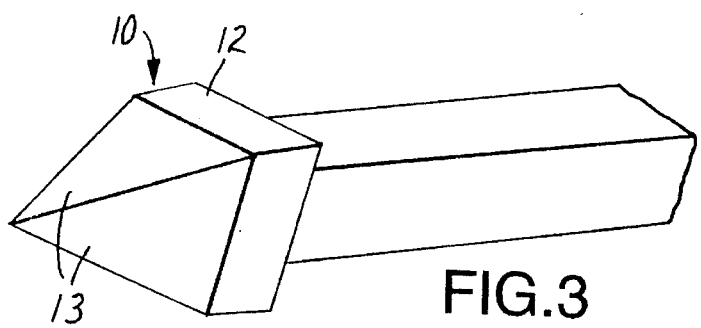
FIG. 3 is a perspective view of a third prior art trocar obturator having portions broken away to show details.

The first structure (structure A) was a generally cylindrical shaped structure. The second structure (structure B) comprised the trigger/protective sleeve structure according to the present invention. See FIG. 11. The third structure (structure C) comprised a structure generally as shown in FIG. 4. Finally, the fourth structure (structure D) comprised a structure generally as shown in FIG. 2, and was taken from a 10 mm Ethicon Endopath™ trocar, generally available from Ethicon of Somerville, N.J. Structures A, B and C were constructed from Lexan HPS #1-1125 polycarbonate, generally available from General Electric (GE).

Referring now to Table 1, the obturator tip shape for use with the above structures was selected as either a triangular (2,3) or triangular, with a flat edge (1,4) (to prevent rotation of the sleeve relative to the obturator). All of the obturator tips were constructed from the same material (ASTM #2024 Aluminum). All of the obturators were sharpened initially.

TABLE 1

| Inner Sheath Shape | A | B | C | D | Material | Tip #, # uses |
|---|---|---|---|---|---|---|
| | | | | 3.15 | Neoprene | 2,1 |
| | 2.35 | | | | Neoprene | 2,2 |
| | | | 2.90 | | Neoprene | 1,1 |
| | 2.20 | | | | Neoprene | 3,2 |
| | | 2.30 | | | Neoprene | 4,2 |
| | | 2.30 | | | Neoprene | 1,2 |
| | 2.30 | | | | Neoprene | 2,5 |
| | 2.15 | | | | Neoprene | 3,4 |
| | | | | 2.70 | Neoprene | 3,5 |
| | | | 3.10 | | Neoprene | 1,5 |
| | | 2.20 | | | Neoprene | 4,6 |
| | | | 3.35 | | Neoprene | 4,7 |
| | | 2.65 | | | Neoprene | 1,8 |
| AVERAGE | 2.25 | 2.36 | 3.12 | 2.93 | | |
| STD DEV | 0.09 | 0.20 | 0.23 | 0.32 | | |
| | | | 6.45 | | Polyurethane | 4,1 |
| | 5.10 | | | | Polyurethane | 3,1 |
| | | 5.70 | | | Polyurethane | 4,3 |
| | | | | 8.60 | Polyurethane | 3,3 |
| | 5.20 | | | | Polyurethane | 2,3 |
| | | 5.40 | | | Polyurethane | 1,3 |
| | | 5.90 | | | Polyurethane | 1,4 |
| | | 6.20 | | | Polyurethane | 4,4 |
| | 5.20 | | | | Polyurethane | 3,6 |
| | | | | 9.30 | Polyurethane | 2,6 |
| | | 6.05 | | | Polyurethane | 1,6 |
| | | | 7.25 | | Polyurethane | 1,7 |
| | 5.15 | | | | Polyurethane | 2,9 |
| AVERAGE | 5.16 | 5.85 | 7.25 | 8.95 | | |
| STD DEV | 0.05 | 0.31 | 0.57 | 0.49 | | |

The test was performed as follows. An Instron brand force testing machine (with a 1000 pound load cell) was selected to measure insertion force. The force was measured in pounds. The obturator and sleeve structures (e.g. A–D) were placed in a generally vertical position and the membrane was placed in a generally horizontal orientation. A fixture was used to fix the relative positions of the obturator and the sleeve structures (A–D). The relative positions of obturator and sleeve structures were manually chosen, but the positions were chosen to approximate the positions of the structure (A–D) relative to the obturator as the trocar is passed through tissue. For example, the end of the cylindrical shaped structure (A) was placed just proximal to the end of the cutting surface of the obturator. Note that no cannula was used in these tests.

The combination sleeve/obturator assembly was moved in a direction normal to the surface of the membrane and toward the membrane at a speed of approximately fifty (50) inches per second. Average Peak Insertion Force test results are shown in Table 2.

TABLE 2

| | Average Peak Insertion Forces (lbs) | | | |
|---|---|---|---|---|
| Shape/Material | A | B | C | D |
| Neoprene | 2.25 | 2.36 | 3.12 | 2.93 |
| Polyurethane | 5.16 | 5.85 | 7.25 | 8.95 |

The Neoprene and Polyurethane membranes were selected to approximate tissue. Additionally, the relative positions of the test structures A–D and the obturator were manually positioned to approximate their orientation as a trocar is passed through tissue. However, factors too numerous to list here may affect the actual insertion force for a trocar. For example, the spring constant of the trocar, the sharpness of the obturator, the interaction of the sleeve/obturator and cannula (note no cannula used in this test), the friction constant of the sleeve, and the size of the obturator may all affect the actual insertion force encountered by a surgeon.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A trocar for placement in the lumen of a cannula to facilitate insertion of the cannula through tissue defining a body cavity, the cannula having a distal end, said trocar comprising:

a handle, an elongate obturator extending from said handle and defining a longitudinal axis, said obturator comprising cutting surfaces for cutting the tissue defining the body cavity, a trigger having portions adapted to project beyond the distal end of the cannula, said trigger having a plurality of tissue cams, each tissue cam comprising an inner surface and an outer, substantially planar surface situated at an angle relative to said longitudinal axis, and a distal end portion that is arcuate about an axis normal to the outer surface, wherein each of said distal end portions has a distal most point, said distal end portions of said tissue cams intersect at edge portions, and said distal most points of said distal end portions are spaced distally from said edge portions.

2. A trocar according to claim 1 wherein the trocar comprises means for restricting rotation of the obturator relative to the trigger.

3. A trocar according to claim 2 wherein said means for restricting rotation of the obturator relative to the trigger comprises a detent member on the trigger, and the obturator having a generally cylindrical base portion with a chamfered edge for engaging the detent member.

4. A trocar according to claim 1 wherein said trigger is mounted around the obturator, and the trocar includes means for affording movement of the trigger longitudinally relative to said obturator, wherein the trocar includes means for affording retraction of the trigger proximally relative to the obturator as the trocar is advanced through the tissue defining the body cavity, and wherein the trocar further includes means for advancing the trigger distally after the cannula has penetrated through the tissue defining the body cavity.

5. A trocar according to claim 4 wherein said trocar includes means for retracting the obturator proximally relative to said cannula after said obturator has cut the tissue defining the body cavity.

6. A trocar according to claim 5 wherein said obturator retracts proximally after said trigger advances distally.

7. A trocar according to claim 1 wherein the lumen of the cannula has a diameter of approximately ten (10) millimeters, and each of the distal end portions of the trigger has a radius of curvature from about 0.18 inches to about 0.32 inches.

8. A trocar according to claim 7 wherein each of the distal end portions of the trigger has a radius of curvature of about 0.25 inches.

9. A trocar according to claim 1 wherein the outer surface of said tissue cam is located at an angle between 10 degrees and 40 degrees relative to the longitudinal axis.

10. A trocar according to claim 9 wherein the outer surface of said tissue cam is located at an angle of 15 degrees relative to the longitudinal axis.

11. A trocar for placement in the lumen of a cannula to facilitate insertion of the cannula through tissue defining a cavity, the cannula having a distal end, said trocar comprising:

a handle, an elongate obturator extending from said handle and defining a longitudinal axis, said obturator comprising cutting surfaces for cutting the tissue defining the body cavity, a protective sleeve having portions adapted to project beyond the distal end of the cannula, said protective sleeve having a plurality of tissue cams, each tissue cam comprising an inner surface and an outer, substantially planar surface situated at an angle relative to said longitudinal axis, and a distal end portion that is arcuate about an axis normal to the outer surface, wherein each of said distal end portions has a distal most point, said distal end portions of said tissue cams intersect at edge portions, and said distal most points of said distal end portions are spaced distally from said edge portions.

12. A trocar according to claim 11 wherein the lumen of the cannula has a diameter of approximately ten (10) millimeters, and each of the distal end portions of the protective sleeve has a radius of curvature from about 0.18 inches to about 0.32 inches.

13. A trocar according to claim 12 wherein wherein each of the distal end portions of the protective sleeve has a radius of curvature of about 0.25 inches.

14. A trocar according to claim 11 wherein the outer surface of said tissue cam is located at an angle between 10 degrees and 40 degrees relative to the longitudinal axis.

15. A trocar according to claim 14 wherein the outer surface of said tissue cam is located at an angle of 15 degrees relative to the longitudinal axis.

16. A trocar according to claim 11 wherein the trocar comprises means for restricting rotation of the obturator relative to the protective sleeve.

17. A trocar for placement in the lumen of a cannula to facilitate insertion of the cannula through tissue defining a body cavity, the cannula having a distal end, said trocar comprising:

a handle, an elongate obturator extending from said handle and defining a longitudinal axis, said obturator comprising cutting surfaces for cutting the tissue defining the body cavity, a protective sleeve having portions adapted to project beyond the distal end of the cannula, said protective sleeve having a plurality of tissue cams, each tissue cam comprising an inner surface and an outer, substantially planar surface situated at an angle relative to said longitudinal axis, and a distal end portion, and wherein each of said distal end portions has a distal most point, said distal end portions of said tissue cams intersect at edge portions, said distal most points of said distal end portions are spaced distally from said edge portions, and each of said distal end portions are arcuate about an axis normal to the outer surface.

* * * * *